(12) United States Patent
Wenzel et al.

(10) Patent No.: US 7,838,477 B2
(45) Date of Patent: Nov. 23, 2010

(54) LIQUID CLEANSER FORMULATION WITH SUSPENDING AND FOAMING CAPABILITIES

(75) Inventors: Scott W. Wenzel, Neenah, WI (US); Corey Cunningham, Larsen, WI (US); Julie M. Utschig, Chicago, IL (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 98 days.

(21) Appl. No.: 11/466,873

(22) Filed: Aug. 24, 2006

(65) Prior Publication Data

US 2008/0051314 A1    Feb. 28, 2008

(51) Int. Cl.
*C11D 1/00* (2006.01)
*C11D 3/37* (2006.01)
*A61K 8/36* (2006.01)

(52) U.S. Cl. .................. 510/121; 510/151; 510/155; 510/419; 510/434; 510/473; 510/475; 510/507; 424/401; 424/485; 424/486; 424/70.11; 424/70.19; 424/70.22; 424/70.31

(58) Field of Classification Search .................. 510/121, 510/151, 155, 419, 434, 473, 475, 507; 424/401, 424/485, 486, 70.11, 70.19, 70.22, 70.31
See application file for complete search history.

(56) References Cited

U.S. PATENT DOCUMENTS

| | | | |
|---|---|---|---|
| 4,022,351 A | 5/1977 | Wright | |
| 4,147,306 A | 4/1979 | Bennett | |
| 4,184,615 A | 1/1980 | Wright | |
| 5,846,549 A | 12/1998 | Beauquey et al. | |
| 6,053,364 A | 4/2000 | van der Heijden | |
| 6,627,585 B1 | 9/2003 | Steer | |
| 6,660,282 B2 | 12/2003 | Crotty et al. | |
| 2001/0006621 A1 | 7/2001 | Coupe et al. | |
| 2003/0191036 A1 | 10/2003 | MacDonald et al. | |
| 2003/0228270 A1* | 12/2003 | Tazberik et al. | .......... 424/70.22 |
| 2005/0049157 A1 | 3/2005 | MacDonald et al. | |
| 2005/0148490 A1 | 7/2005 | Krzysik et al. | |
| 2005/0227880 A1* | 10/2005 | Shiloach et al. | ............ 510/130 |

FOREIGN PATENT DOCUMENTS

| | | | |
|---|---|---|---|
| EP | 323209 | * | 7/1989 |
| EP | 0339539 A2 | | 11/1989 |
| EP | 0407187 A2 | | 1/1991 |
| JP | 2004/262805 | | 9/2004 |
| WO | 03/095600 A1 | | 11/2003 |

OTHER PUBLICATIONS

National Starch & Chemical, "Structure Plus" (Product Information), Feb. 2001.
Noveon, "Carbopol Aqua SF-1 Polymer Product Summary Sheet," 2002, Nov. 2002.
International Search Report and Written Opinion from PCT/IB2007/052902, dated Mar. 26, 2008.

* cited by examiner

*Primary Examiner*—Brian P Mruk
(74) *Attorney, Agent, or Firm*—Armstrong Teasdale LLP

(57) ABSTRACT

The present disclosure generally relates to cleansing products for cleansing the skin and hair. More particularly, the present disclosure relates to liquid cleansing compositions that have a sufficient viscosity to maintain particles suspended in the cleanser, but that may also be used with suitable dispensers, such as pump foam dispensers, to generate foam.

16 Claims, 1 Drawing Sheet

LIQUID CLEANSER FORMULATION WITH SUSPENDING AND FOAMING CAPABILITIES

BACKGROUND OF DISCLOSURE

The present disclosure generally relates to cleansing products for cleansing the skin and hair. More particularly, the present disclosure relates to liquid cleansing compositions that have a sufficient viscosity to maintain particles suspended in the cleanser, but that may also be used with suitable dispensers, such as pump foam dispensers, to generate foam.

For aesthetic and marketing reasons, it is often desirable for liquid cleansing compositions to be foamable. Consumers often associate foaming cleansers with a better cleansing effect, and a feeling that the cleanser is "working" better than a non-foaming cleanser. Consequently, it is advantageous for a cleanser to be capable of producing voluminous foam when used in connection with either a dispenser, such as a pump foam dispenser, or when shear is applied, such as when rubbed between hands during hand washing.

However, delivery of liquid cleansing compositions through foam producing dispensers has presented many challenges. For instance, it is often desirable for cleansers to include additives such as moisturizers, anti-bacterials, and other skin or hair benefit agents, in addition to cleansing surfactants. However, such additives can interfere with the ability of the composition to foam. Furthermore, certain types of foam-producing dispensers that use porous filters or meshed screens to produce foam may not work well (or at all) with even moderately viscous compositions. Consequently, foamable cleansing compositions currently on the market are water-thin and easily pumped through a foam-producing pump head. However, such water-thin cleansers do not have the capability to suspend particulate additives evenly throughout the cleanser and still produce the volume of foam desired by consumers.

The present disclosure addresses the problems associated with currently available foamable liquid cleansers by providing a cleansing composition with sufficient viscosity to suspend particulate additives relatively homogenously throughout the cleanser, but that may still be used effectively in conjunction with a pump foam dispenser.

SUMMARY OF THE DISCLOSURE

The present disclosure is directed to liquid cleansing compositions. The cleansers may be used in connection with a suitable dispenser, such as a pump foam dispenser, to produce foam. Due to the composition and viscosity of the cleansers, particulate additives may be suspended throughout the cleanser.

In one aspect, the present disclosure is directed to a cleansing composition comprising from about 0.1% (by weight) to about 40% (by weight) of a foaming agent, from about 0.01% (by weight) to about 5% (by weight) of a thickener, and from about 0.01% (by weight) to less than about 5% (by weight) of a swellable clay.

In another aspect, the present disclosure is directed to a composition comprising from about 0.01% (by weight) to about 5% (by weight) of a thickener, from about 0.01% (by weight) to about 10% (by weight) of a swellable clay, and having a viscosity of from about 1,000 cps to less than about 50,000 cps.

Other objects and features will be in part apparent and in part pointed out hereinafter.

DETAILED DESCRIPTION OF THE DISCLOSURE

Figure 1:
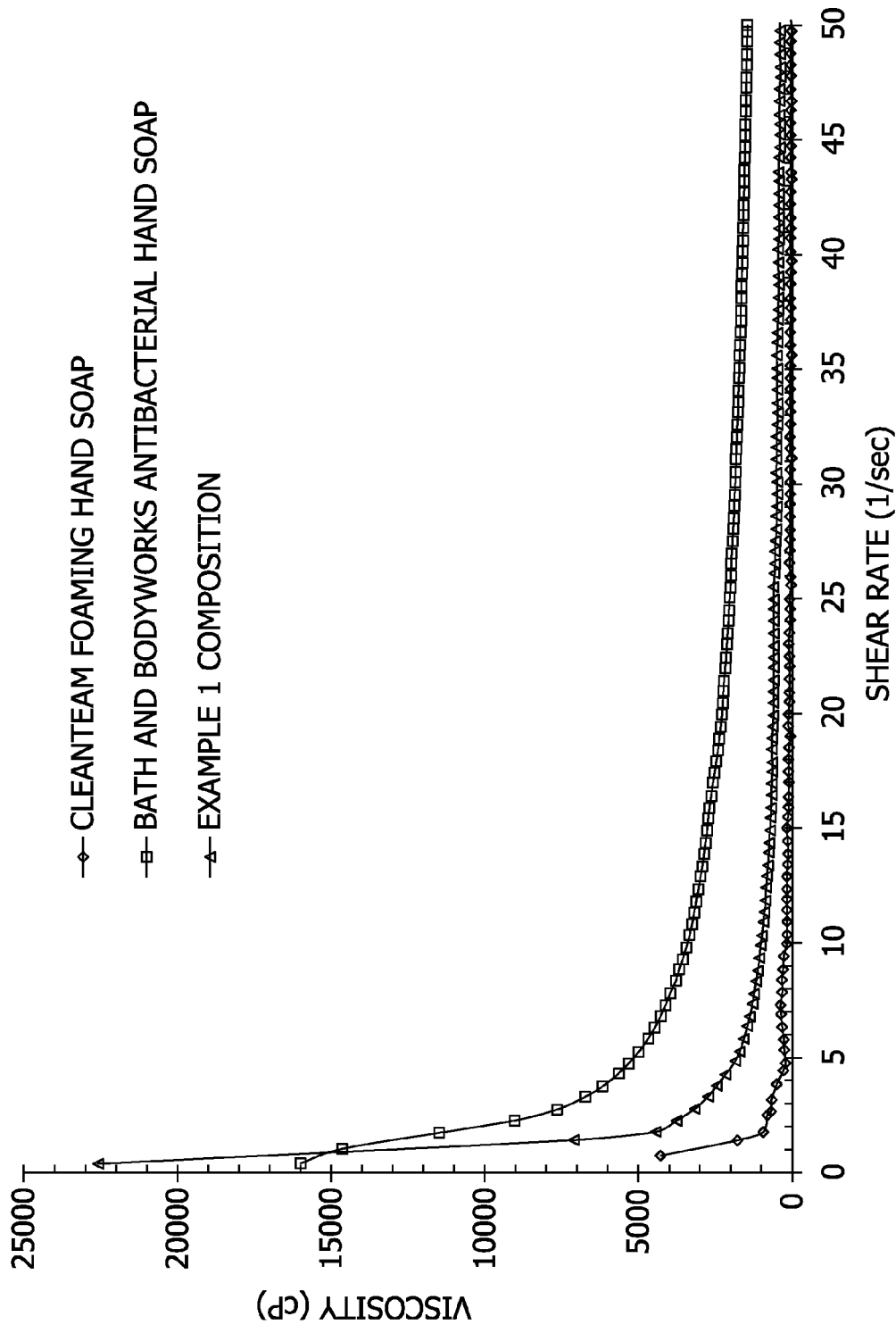
FIG. 1 shows a graph depicting the viscosity under various shear rates of a composition of the present invention, a commercially available suspended bead hand soap, and a commercially available foaming hand soap, as discussed in Example 5.

The present disclosure is generally directed to cleansing compositions, such as hand soaps, body soaps, body washes, shampoos, surface cleaners, dish soap, facial cleansers, hand washes, hand sanitizers, cleansing systems, etc. The cleansing compositions described herein may include a foaming agent, such as a surfactant, a thickener, and a swellable clay. Due to the composition and viscosity of the cleansers, particulate material, such as skin or hair benefit additives and/or colored particles, may be suspended in the cleansing compositions. Additionally, the cleansing compositions may be used in conjunction with a suitable dispenser, such as a pump foam dispenser, to generate foam upon dispensing and/or upon the application of shear, such as when the cleansing composition is rubbed between hands during hand washing.

Although discussed herein primarily in terms of cleansing compositions, it should be understood that the compositions of the present invention may comprise other foamable liquid compositions, and need not comprise a surfactant. For example, in certain embodiments, the compositions of the present invention may comprise a thickener, a swellable clay, a foaming agent (which may or may not comprise a surfactant), and optionally a solvent or other carrier material. Examples of such products include, for example, hand sanitizers, lotions, anti-microbial treatments, facial treatments, exfoliants, and the like.

As discussed above, it may be desirable to incorporate particulate material, such as skin or hair benefit additives and/or coloring agents, into cleansing compositions. However, in order to maintain particles suspended throughout the composition, the composition needs to be sufficiently thick and viscous. If the composition is too thin or has an insufficient viscosity, instead of remaining suspended, the particles will settle out of the composition and will not be dispensed to a user with the dispensed portion of the composition. A thickness and viscosity sufficient to maintain particles suspended in a composition may be achieved by including thickeners in the composition. Currently available cleansing compositions that are capable of suspending particles therein generally include relatively large amounts of thickeners. As a result, these compositions have a moderate to high viscosity and thickness. However, as discussed above, pump foam dispensers are oftentimes incompatible with moderately or highly viscous compositions. Consequently, compositions capable of maintaining particles suspended therein have not previously been successfully used with pump foam dispensers.

Advantageously, it has now been discovered that liquid cleansing products may be formulated that are capable of maintaining particles suspended therein for extended periods of time, while still being compatible for use with pump foam dispensers. More particularly, the combination of thickeners and swellable clay in the compositions of the present invention give the compositions sufficient shear-thinning properties to allow the composition to move through the foam producing head of a pump foam dispenser, while still maintaining particles suspended in the composition. Without wishing to be bound to any particular theory, it is believed that the swellable clay acts to increase the yield value and zero-shear viscosity of the composition, which in turn allows for a lower amount of thickener to be included (thus resulting in a lower composition viscosity), as compared to currently available products and compositions that do not comprise swellable clay, while maintaining the particle suspending capabilities of the composition. Furthermore, because of the thixotropic nature of the swellable clay, the viscosity of the composition is reduced when the composition is subject to shear, thus allowing the composition to pass through a foam pump dispenser.

As noted above, the cleansing products of the present invention may comprise a foaming agent, such as a surfactant, as well as a thickener, and a swellable clay. Upon dispensing the cleanser from a pump-type or other similar dispenser and/or upon application of shear, the cleansing product will produce foam that may be used for cleansing applications. Although discussed primarily in terms of a surfactant, it is to be understood that the foaming agent may be an agent other than a surfactant. For example, alternately or in addition to surfactants, the foaming agent may comprise emulsifiers, ethoxylated skin conditioning agents, solubilizers, derivatized silicone polymers, and combinations thereof. Typically, the cleanser comprises a foaming agent in an amount of from about 0.1% (by weight) to about 40% (by weight), more preferably about 0.3% (by weight) to about 25% (by weight), and still more preferably about 0.5% (by weight) to about 15% (by weight). The foaming agent is included in the cleansing composition to provide a cleaning, lathering, and/or foaming action during use of the product.

As used herein, "by weight" refers to the total weight of the composition. For example, if the cleansing composition has a total weight of 100 grams and comprises 40% (by weight) foaming agent, the cleansing composition comprises 40 grams of foaming agent. As will be recognized by those skilled in the art, some commercially available surfactants (and thickeners or other composition components) are sold as a solution; e.g., a certain percentage of surfactant in water. If such a solution is used to formulate a composition of the present invention, it is to be understood that the percent (by weight) of the surfactant (or other component) given herein is referring to the percent (by weight) of the actual surfactant (or other component) in the final composition, not the percent (by weight) of the surfactant plus water solution.

Suitable surfactants for use in the cleansing composition include anionic surfactants, amphoteric surfactants, cationic surfactants, zwitterionic surfactants, non-ionic surfactants, and combinations thereof.

Suitable anionic surfactants include, for example, alkyl sulfates, alkyl ether sulfates, alkyl aryl sulfonates, alpha-olefin sulfonates, alkali metal or ammonium salts of alkyl sulfates, alkali metal or ammonium salts of alkyl ether sulfates, alkyl phosphates, silicone phosphates, alkyl glyceryl sulfonates, alkyl sulfosuccinates, alkyl taurates, acyl taurates, alkyl sarcosinates, acyl sarcosinates, sulfoacetates, alkyl phosphate esters, mono alkyl succinates, monoalkyl maleates, sulphoacetates, acyl isethionates, alkyl carboxylates, phosphate esters, sulphosuccinates (e.g., sodium dioctylsulphosuccinate), and combinations thereof. Specific examples of anionic sufactants include sodium lauryl sulphate, sodium lauryl ether sulphate, ammonium lauryl sulphosuccinate, ammonium lauryl sulphate, ammonium lauryl ether sulphate, sodium dodecylbenzene sulphonate, triethanolamine dodecylbenzene sulphonate, sodium cocoyl isethionate, sodium lauroyl isethionate, sodium N-lauryl sarcosinate, and combinations thereof.

Suitable cationic surfactants include, for example, alkyl ammonium salts, polymeric ammonium salts, alkyl pyridinium salts, aryl ammonium salts, alkyl aryl ammonium salts, silicone quaternary ammonium compounds, and combinations thereof. Specific examples of cationic surfactants include behenyltrimonium chloride, stearlkonium chloride, distearalkonium chloride, chlorhexidine diglutamate, polyhexamethylene biguanide (PHMB), cetyl pyridinium chloride, benzammonium chloride, benzalkonium chloride, and combinations thereof.

Suitable amphoteric surfactants include, for example, betaines, alkylamido betaines, sulfobetaines, N-alkyl betaines, sultaines, amphoacetates, amophodiacetates, imidazoline carboxylates, sarcosinates, acylamphoglycinates, such as cocamphocarboxyglycinates and acylamphopropionates, and combinations thereof. Specific examples of amphoteric surfactants include cocamidopropyl betaine, lauramidopropyl betaine, meadowfoamamidopropyl betaine, sodium cocoyl sarcosinate, sodium cocamphoacetate, disodium cocoamphodiacetate, ammonium cocoyl sarcosinate, sodium cocoamphopropionate, and combinations thereof.

Suitable zwitterionic surfactants include, for example, alkyl amine oxides, silicone amine oxides, and combinations thereof. Specific examples of suitable zwitterionic surfactants include, for example, 4-[N,N-di(2-hydroxyethyl)-N-octadecylammonio]-butane-1-carboxylate, S-[S-3-hydroxypropyl-5-hexadecylsulfonio]-3-hydroxypentane-1-sulfate, 3-[P,P-diethyl-P-3,6,9-trioxatetradexopcylphosphonio]-2-hydroxypropane-1-phosphate, 3-[N,N-dipropyl-N-3-dodecoxy-2-hydroxypropylammonio]-propane-1-phosphonate, 3-(N,N-dimethyl-N-hexadecylammonio)propane-1-sulfonate, 3-(N,N-dimethyl-N-hexadecylammonio)-2-hydroxypropane-1-sulfonate, 4-[N,N-di(2-hydroxyethyl)-N-(2-hydroxydodecyl)ammonio]-butane-1-carboxylate, 3-[S-ethyl-S-(3-dodecoxy-2-hydroxypropyl)sulfonio]-propane-1-phosphate, 3-[P,P-dimethyl-P-dodecylphosphonio]-propane-1-phosphonate, 5-[N,N-di(3-hydroxypropyl)-N-hexadecylammonio]-2-hydroxy-pentane-1-sulfate, and combinations thereof.

Suitable non-ionic surfactants include, for example, mono- and di-alkanolamides such as, for example, cocamide MEA and cocamide DEA, amine oxides, alkyl polyglucosides, ethoxylated silicones, ethoxylated alcohols, ethoxylated carboxylic acids, ethoxylated amines, ethoxylated amides, ethoxylated alkylolamides, ethoxylated alkylphenols, ethoxylated glyceryl esters, ethoxylated sorbitan esters, ethoxylated phosphate esters, glycol stearate, glyceryl stearate, and combinations thereof. It will be recognized by one skilled in the art that many of the nonionic surfactants described herein may act to improve the foaming properties of the product, and may provide a more compact, reduced bubble size or creamy foam.

The compositions of the present invention may also comprise a thickener, which acts to thicken or increase the viscosity of the composition. Typically, the composition will comprise from about 0.01% (by weight) to about 5% (by weight) of thickener.

A variety of thickeners may be used in the compositions described herein. In one embodiment, the thickener may be a cellulosic thickener or gum. Examples of suitable cellulosic or gum thickeners include xanthan gum, agar, alginates, carrageenan, furcellaran, guar, cationic guar, gum arabic, gum tragacanth, karaya gum, locust bean gum, dextran, starch, modified starches, gellan gum, carboxymethylcellulose, hydroxypropylcellulose, hydroyethylcellulose, propylene glycol alginate, hydroxypropyl guar, amylopectin, cellulose gum, chitosan, modified chitosan, hydroxypropyl methylcellulose, microcrystalline cellulose, silica, fumed silica, colloidal silica, dehydroxanthan gum, non-acrylic based carbomers, and combinations thereof. When the thickener is a cellulosic or gum thickener, the thickener is preferably present in the cleansing composition in an amount of from about 0.01% (by weight) to about 2% (by weight), and more preferably in an amount of from about 0.1% (by weight) to about 1% (by weight).

Alternately or in addition, the thickener may be an acrylic based polymer. Non-limiting examples of suitable acrylic based polymer thickeners include acrylates/$C_{10}$-$C_{30}$ alkyl acrylate crosspolymers, certain carbomers, acrylates copolymers, aminoacrylates copolymers, and combinations thereof. Examples of commercially available acrylic based polymer thickeners include Structure® Plus (National Starch & Chemical, Bridgewater, N.J.), which is an acrylates/aminoacrylates/$C_{10-30}$ alkyl PEG-20 itaconate copolymer, Carbopol® Aqua SF-1 Polymer (Noveon, Cleveland Ohio), which is an acrylates copolymer, Pemulen® TR-1 and TR-2 and Carbopol® ETD 2020 (available from Noveon), which are acrylates/C10-30 alkyl acrylates crosspolymers, and the Carbopol® Ultrez series of polymers (available from Noveon), which are carbomers. When the thickener is an acrylic based polymer, the thickener is preferably present in the composition in an amount of from about 0.1% (by weight) to about 5% (by weight).

The cleansers of the present invention may optionally be formulated using an acid-sensitive thickener and/or a base-sensitive thickener. As the names suggest, acid-sensitive thickeners are activated (i.e., swell or "thicken") upon contact with an acidic agent, while base-sensitive thickeners are activated upon contact with an alkaline agent. One advantage of using acid and/or base sensitive thickeners in the compositions of the present invention is improved ease of formulation. For instance, acid or base sensitive thickeners may be more readily dispersed in a formulation when in a non-activated state than when in an activated (or "thickened") state. Thus, an acid- or base-sensitive thickener may be combined with other formulation components prior to activation, and activated by contact with an acidic or alkaline agent after the acid- or base-sensitive thickener is dispersed throughout the formulation. This process is illustrated in Examples 1 and 2 of the present disclosure.

Examples of suitable acid-sensitive thickeners for use in the compositions of the present disclosure include the Structure® Plus (National Starch & Chemical, Bridgewater, N.J.) thickener, described above. The acid-sensitive thickeners may be activated by contact with any of a wide range of acidic agents including, for example, glycolic acid, lactic acid, phosphoric acid, citric acid, other organic acids, and similar acidic agents. Acid sensitive thickeners are generally activated over a pH range of from about 3 to about 9, and more typically over a pH range of from about 3 to about 7. The Structure® Plus thickener is typically activated over a pH range of from about 3 to about 9.

Examples of suitable base-sensitive thickeners include the Carbopol® Aqua SF-1 Polymer (Noveon, Cleveland Ohio) thickener, described above, as well as the Pemulen® TR-1 and TR-2 thickeners (available from Noveon), the Carbopol® ETD 2020 thickeners (available from Noveon), and the Carbopol® Ultrez series of thickeners (available from Noveon), all described above, and other carbomers and starches, and combinations thereof. The base-sensitive thickeners may be activated by contact with any of a wide range of alkaline agents including, for example, various metal hydroxides and amines, and other similar alkaline agents. Non-limiting examples of suitable metal hydroxides include potassium hydroxide and sodium hydroxide. Non-limiting examples of suitable amines include triethanolamine, diethanolamine, monoethanolamine, tromethamine, aminomethylpropanol, triisopropanolamine, diisopropanolamine, tetrahydroxypropylethylenediamine, and PEG-15 cocoamine. Base sensitive thickeners are generally activated over a pH range of from about 5 to about 11, and more typically over a pH range of from about 6 to about 11.

In certain embodiments, the compositions of the present invention may comprise two or more different types of thickeners. For instance, the compositions of the present invention may comprise any combination of cellulosic thickeners, gum thickeners, acid-sensitive thickeners, base-sensitive thickeners, and/or acrylic based polymer thickeners.

In certain embodiments, an acid-sensitive thickener may be used in combination with a base-sensitive thickener. For instance, a composition comprising both an acid-sensitive thickener and a base-sensitive thickener may be formulated by adding the acid-sensitive and base-sensitive thickeners to the formulation in their non-activated states and then activating first one and then the other thickener. For example, once the thickeners are dispersed in the formulation, the pH of the formulation may be lowered by adding a sufficient amount of an acid to activate the acid-sensitive thickener. Once the acid-sensitive thickener is "activated," the pH may be raised by adding a sufficient amount of an alkaline agent to activate the base-sensitive thickener. Alternately, the base-sensitive thickener may be activated first, followed by activation of the acid-sensitive thickener. Other methods of formulating compositions comprising an acid-sensitive thickener and a base-sensitive thickener may also be used.

The products of the present invention additionally comprise a swellable clay. The swellable clay acts as a thixotropic agent, giving the composition its shear-thinning properties, while allowing the composition to remain sufficiently viscous to suspend particles therein when under low or no shear.

A variety of clays are suitable for use in the compositions described herein including, for example, bentonite, laponite, hectorite, montmorillonite, beidelite, saponite, stevensite, magnesium aluminum silicate, other aluminum silicates, as well as various other natural and/or synthetic clays, and combinations thereof. Typically, the composition will comprise from about 0.01% (by weight) to about 10% (by weight) and more preferably from about 0.1% (by weight) to about 5% (by weight) of a swellable clay. In one embodiment, the composition may comprise from about 0.01% (by weight) to less than about 5% (by weight) of a swellable clay.

As discussed above, the compositions of the present invention may optionally further comprise particles suspended therein. Advantageously, the compositions of the present disclosure have sufficient yield value and viscosity to allow particles to remain suspended throughout the composition over extended periods of time, without significant settling. The particles may thus remain dispersed relatively homogenously throughout the composition. For purposes of the present disclosure, particles are considered to be suspended in the composition if there is no visual presence of the particles settled on the bottom of the container or dispenser for a reasonable amount of time, e.g., for about 3 months.

Particles included in the compositions of the present invention may be of several types. As discussed herein, the compositions of the present invention may be used in conjunction with a pump-type dispenser, and in particular, a pump foam dispenser. Depending on the size of the particles suspended in the composition, when the dispenser is pumped, the particles may either remain in the dispenser with the bulk of the composition or, alternately, may be delivered through the pump head with the dispensed portion of the composition.

The ability of the particles to pass through the pump head is dependent on particle size. For instance, conventional pump foam dispensers create foam by passing surfactant compositions through porous filters or mesh screens. Particles smaller than the pore size of the filters or screens will be able to pass through the pump head, while particles larger than the pore size of the filter or screen will be retained in the dispenser. Particles capable of passing through a typical pump foam dispenser head are referred to herein as "pumpable" particles. The pumpable particles of the present invention will typically have a particle size of from about 1 nanometer to about 300 microns, and more preferably from about 500 nanometers to about 10 microns.

In one embodiment, the size of the pumpable particles may be selected based on the minimum diameter of a mesh or filter screen that can be used with a foam pump dispenser head. For instance, for pumpable particles, the ratio of this minimum diameter to particle size is preferably at least about 2:1. In certain embodiments, the ratio of minimum diameter to particle size may be from about 2:1 to about 80,000:1, and more preferably from about 5:1 to about 250:1, more preferably from about 10:1 to about 200:1, and more preferably from about 15:1 to about 150:1. Generally speaking, however, the pumpable particles will have a particle size equal to or less than the minimum diameter of the mesh or filter screen.

Particles that are not capable of passing through a typical pump foam dispenser head and that are retained in the dispenser with the bulk of the composition are referred to herein as "non-pumpable" particles. Preferably, the non-pumpable particles have a particle size of from about 150 microns to about 4 millimeters, and more preferably from about 300 microns to about 4 millimeters.

As noted above, the compositions of the present invention may be used in conjunction with pump-type dispensers such as pump foam dispensers. Such dispensers typically comprise a dip tube that extends from the pump engine into the bulk of the composition to be pumped. Thus, in one embodiment, when the composition of the present invention is used in combination with such a dispenser, the size of the non-pumpable particles may be selected based on the minimum diameter of the dip tube. In this embodiment, the non-pumpable particles will generally have a particle size greater than the diameter of the dip tube.

As noted above, the particles (whether pumpable or non-pumpable) may comprise various additives, such as skin or hair benefit agents, and/or may be colored particles. The additives may be included in the composition in encapsulated and/or in unencapsulated form.

A variety of different additives may suitably be included in the compositions of the present disclosure in encapsulated or unencapsulated form including, for example, moisturizing agents, antioxidants, fragrances, antimicrobials, sunscreen actives, conditioning agents, botanicals, vitamins, proteins, silicones, alpha-hydroxy acids such as salicylic acid, melamine-formaldehyde particles, preservatives, and combinations thereof. Such additives (whether or not encapsulated) may be "pumpable" particles and/or may be "non-pumpable" particles. In one preferred embodiment, additives such as fragrances, antimicrobials, and/or other additives that have a beneficial effect on skin or hair may be incorporated into pumpable particles, so that they are dispensed through the pump head and may be contacted with the skin and/or hair of a user. Optionally, particles may be formulated to comprise more than one type of additive in an individual particle.

In one embodiment, the particles may be colored particles. The colored particles may comprise a coloring agent, such as dyes, color additives, pigments, and/or lakes that may be included in the composition in unencapsulated form or optionally may be encapsulated, as described herein, in a suitable encapsulant. Suitable dyes include, for example, Blue 1, Blue 4, Brown 1, External Violet 2, External Violet 7, Green 3, Green 5, Green 8, Orange 4, Orange 5, Orange 10, Orange 11, Red 4, Red 6, Red 7, Red 17, Red 21, Red 22, Red 27, Red 28, Red 30, Red 31, Red 33, Red 34, Red 36, Red 40, Violet 2, Yellow 5, Yellow 6, Yellow 7, Yellow 8, Yellow 10, Yellow 11, Acid Red 195, Anthocyanins, Beetroot Red, Bromocresol Green, Bromothymol Blue, Capsanthin/Capsorubin, Curcumin, and Lactoflavin.

Suitable color additives include, for example, aluminum powder, annatto, bismuth citrate, bismuth oxychloride, bronze powder, caramel, carmine, beta carotene, chloraphyllin-copper complex, chromium hydroxide green, chromium oxide greens, copper powder, disodium EDTA-copper, ferric ammonium ferrocyanide, ferric ferrocyanide, guauazulene, guanine, henna, iron oxides, lead acetate, manganese violet, mica, pyrophylite, silver, titanium dioxide, ultramarines, zinc oxide, and combinations thereof.

Suitable pigments or lakes include, for example, Blue 1 Lake, External Yellow 7 Lake, Green 3 Lake, Orange 4 Lake, Orange 5 Lake, Orange 10 Lake, Red 4 Lake, Red 6 Lake, Red 7 Lake, Red 21 Lake, Red 22 Lake, Red 27 Lake, Red 28 Lake, Red 30 Lake, Red 31 Lake, Red 33 Lake, Red 36 Lake, Red 40 Lake, Yellow 5 Lake, Yellow 6 Lake, Yellow 7 Lake, Yellow 10 Lake, and combinations thereof.

In another embodiment, the particle may be a colored bead, such as a particulate polymeric material to which a coloring agent is attached, or added. Optionally, the colored particle may comprise a colored encapsulant, in which one or more additives may optionally be encapsulated. Examples of colored encapsulants include the LipoSpheres™ and LipoBeads™ products described below. In one preferred embodiment, the colored particles are non-pumpable particles that remain in the composition to provide color to the composition.

As noted above, in certain embodiments, the additives may be encapsulated in an encapsulant, such as a shell material or polymer matrix, prior to being formulated into the composition. Micro or nano capsules may be used to gradually release the additive upon an increase in temperature or physical contact, such as when the composition is contacted with the skin of a user. Suitable encapsulation shell or matrix materials include cellulose-based polymeric materials (e.g., ethyl cellulose), carbohydrate-based materials (e.g., cationic starches and sugars), polyglycolic acid, polylactic acid, and lactic acid-based aliphatic polyesters, and materials derived therefrom (e.g., dextrins and cyclodextrins) as well as other materials compatible with human tissues.

The micro or nano encapsulation shell thickness may vary depending upon the composition's formulation, and is generally manufactured to allow the encapsulated additive to be covered by a thin layer of encapsulation material, which may be a monolayer or thicker laminate layer, or may be a composite layer. The encapsulation layer should be thick enough to resist cracking or breaking of the shell during handling or shipping of the product. The encapsulation layer should be constructed such that humidity from atmospheric conditions during storage, shipment, or wear will not cause a breakdown of the microencapsulation layer and result in a release of the composition or component.

Micro and nano encapsulants suitable for use in producing the particles of the present invention may also be commercially obtained. For example, LipoBeads™ products (available from Lipo Technologies, Inc.) are colored beads of a uniform spherical semi-solid matrix of lactose or mannitol microcrystalline cellulose and hydroxypropyl methyl cellulose that may contain hydrophilic or hydrophobic core materials, such as vitamins, natural oils, and antibacterial agents, among others. LipoBeads™ may have an average size of either 700 microns or 1500 microns. LipoSphere™ products (available from Lipo Technologies, Inc.) comprise multiple droplets of hydrophobic and/or hydrophilic material entrapped in a polymer matrix of alginate, agar, or gelatin. The LipoSphere™ products may have a size of from 400 to 4000 microns. LipoCapsule™ gelatin products (available from Lipo Technologies, Inc.) consist of a clear, non-pigmented shell surrounding a hydrophobic core material. The shell may be comprised of gelatin, polyoxymethylene urea, or methoxymethyl methylol melamine. The LipoCapsule™ products may have a size of from 5 to 3000 microns. Other commercially available encapsulated particles include NanoSal™ nanospheres, which are solid hydrophobic nanospheres having an average particle size of 0.01 to 1 micron, which may be used to encapsulate a variety of additives.

The compositions of the present invention may comprise pumpable particles, non-pumpable particles, and combinations thereof. In one embodiment, the composition may comprise pumpable and/or non-pumpable particles, wherein all the particles comprise one or more type of additive. In another embodiment, the composition may comprise pumpable and/or non-pumpable particles, wherein the particles are colored particles. In another embodiment, the composition comprises pumpable and/or non-pumpable particles wherein a portion of the particles are colored and a portion of the particles comprise one or more additive. In one embodiment, a portion of the particles in the composition may comprise one additive and one or more different portions of the particles in the composition may comprise one or more different additives. Other combinations of particle types may also be included in the compositions of the present disclosure.

The amount of particles included in the compositions of the present disclosure will typically vary depending on the type of particle, but preferably are present in an amount of from about 0.01% (by weight) to about 40% (by weight). If the particles are unencapsulated or encapsulated additives, preferred amounts of the additives will vary depending on the type of additive, and may be included in amounts effective to accomplish the intended purpose of the additive. For example, if a particle (e.g., an encapsulated additive) comprises 40% of a sunscreen additive by weight of the particle and the particle is present in the composition in an amount of 10% by weight, the active level of sunscreen additive in the composition would be 4% by weight of the final composition. If the particles are colored particles, such as particles comprising visual beads and/or colored encapsulants, the particles are preferably present in the composition in an amount of from about 0.01% (by weight) to about 10% (by weight), more preferably from about 0.05% (by weight) to about 5% (by weight), and still more preferably from about 0.1% (by weight) to about 3% (by weight).

Alternately or in addition to the particles described herein, the compositions of the present disclosure may have suspended therein non-particulate solids. Examples of non-particulate solids that may be included in the compositions of the present invention include, for example, glitter, ultra fine powders such as micronized zinc oxide, titanium oxide and/or other minerals, ground nut shells, polyethylene and other polymers formed into shapes, and combinations thereof. Preferably, the non-particulate solids are included in the compositions in an amount of from about 0.01% (by weight) to about 25% (by weight).

In one embodiment of the present invention, along with the foaming agent, thickener, swellable clay, and optionally the particles, the composition of the present invention may have suspended therein a secondary phase of components having a different hydrophilicity. For example, the composition may have suspended therein a lipid phase in an amount of from about 0.5% (by weight) to about 15% (by weight), and more preferably from about 2% (by weight) to about 8% (by weight). Typically the lipid phase will be present in the composition in the form of droplets of oils or other components suspended throughout the composition. By applying shear to the composition comprising the suspended lipid phase, such as through use of the composition with a pump foam dispenser as described herein, a foaming lotion is produced. Optionally, such a composition may also have pumpable and/or non-pumpable particles suspended therein.

The lipid phase may comprise components suitable for formulation of a lotion. For example, the lipid phase may include various components, such as for example, natural and/or synthetic fats or oils, silicones, polyethylene glycol, polyols, ethoxylated glycols, esters, glycerin, fatty alcohols, waxes, hydrogenated hydrocarbons solubilizers, moisturizers, cleaning agents, other emollients, and/or the like.

The term "natural fat or oil" is intended to include fats, oils, essential oils, essential fatty acids, non-essential fatty acids, phospholipids, and combinations thereof. Suitable fats and oils include Apricot Kernel Oil, Avocado Oil, Babassu Oil, Borage Seed Oil, Butter, C12-C18 Acid Triglyceride, Camellia Oil, Canola Oil, Caprylic/Capric/Lauric Triglyceride, Caprylic/Capric/Linoleic Triglyceride, Caprylic/Capric/Stearic Triglyceride, Caprylic/Capric Triglyceride, Carrot Oil, Cashew Nut Oil, Castor Oil, Cherry Pit Oil, Chia Oil, Cocoa Butter, Coconut Oil, Cod Liver Oil, Corn Germ Oil, Corn Oil, Cottonseed Oil, C10-C18 Triglycerides, Egg Oil, Epoxidized Soybean Oil, Evening Primrose Oil, Glyceryl Triacetyl Hydroxystearate, Glyceryl Triacetyl Ricinoleate, Glycosphingolipids, Grape Seed Oil, Hazelnut Oil, Human Placental Lipids, Hybrid Safflower Oil, Hybrid Sunflower Seed Oil, Hydrogenated Castor Oil, Hydrogenated Castor Oil Laurate, Hydrogenated Coconut Oil, Hydrogenated Cottonseed Oil, Hydrogenated C12-C18 Triglycerides, Hydrogenated Fish Oil, Hydrogenated Lard, Hydrogenated Menhaden Oil, Hydrogenated Mink Oil, Hydrogenated Orange Roughy Oil, Hydrogenated Palm Kernel Oil, Hydrogenated Palm Oil, Hydrogenated Peanut Oil, Hydrogenated Shark Liver Oil, Hydrogenated Soybean Oil, Hydrogenated Tallow, Hydrogenated Vegetable Oil, Lanolin and Lanolin Derivatives, Lard, Lauric/Palmitic/Oleic Triglyceride, Lesquerella Oil, Linseed Oil, Macadamia Nut Oil, Maleated Soybean Oil, Meadowfoam Seed Oil, Menhaden Oil, Mink Oil, Moringa Oil, Mortierella Oil, Neatsfoot Oil, Oleic/Linoleic Triglyceride, Oleic/Palmitic/Lauric/Myristic/Linoleic Triglyceride, Oleostearine, Olive Husk Oil, Olive Oil, Omental Lipids, Orange Roughy Oil, Palm Kernel Oil, Palm Oil, Peach Kernel Oil, Peanut Oil, Pengawar Djambi Oil, Pentadesma Butter, Phospholipids, Pistachio Nut Oil, Placental Lipids, Rapeseed Oil, Rice Bran Oil, Safflower Oil, Sesame Oil, Shark Liver Oil, Shea Butter, Soybean Oil, Sphingolipids, Sunflower Seed Oil, Sweet Almond Oil, Tall Oil, Tallow, Tribehenin, Tricaprin, Tricaprylin, Triheptanoin, Trihydroxymethoxystearin, Trihydroxystearin, Triisononanoin, Triisostearin, Trilaurin, Trilinolein, Trilinolenin, Trimyristin, Trioctanoin, Triolein, Tripalmitin, Trisebacin, Tristearin, Triundecanoin, Vegetable Oil, Walnut Oil, Wheat Bran Lipids, Wheat Germ Oil, Zadoary Oil, oil extracts of various other botanicals, and other vegetable or partially hydrogenated vegetable oils, and the like, as well as mixtures thereof.

Suitable fatty acids include Arachidic Acid, Arachidonic Acid, Behenic Acid, Capric Acid, Caproic Acid, Caprylic Acid, Coconut Acid, Corn Acid, Cottonseed Acid, Hydrogenated Coconut Acid, Hydrogenated Menhaden Acid, Hydrogenated Tallow Acid, Hydroxystearic Acid, Isostearic Acid, Lauric Acid, Linoleic Acid, Linolenic Acid, Linseed Acid, Myristic Acid, Oleic Acid, Palmitic Acid, Palm Kernel Acid, Pelargonic Acid, Ricinoleic Acid, Soy Acid, Stearic Acid, Tall Oil Acid, Tallow Acid, Undecanoic Acid, Undecylenic Acid, Wheat Germ Acid, and the like, as well as mixtures thereof.

Suitable essential oils include Anise Oil, Balm Mint Oil, Basil Oil, Bee Balm Oil, Bergamot Oil, Birch Oil, Bitter Almond Oil, Bitter Orange Oil, Calendula Oil, California Nutmeg Oil, Caraway Oil, Cardamom Oil, Chamomile Oil, Cinnamon Oil, Clary Oil, Cloveleaf Oil, Clove Oil, Coriander Oil, Cypress Oil, Eucalyptus Oil, Fennel Oil, Gardenia Oil, Geranium Oil, Ginger Oil, Grapefruit Oil, Hops Oil, Hyptis Oil, Indigo Bush Oil, Jasmine Oil, Juniper Oil, Kiwi Oil, Laurel Oil, Lavender Oil, Lemongrass Oil, Lemon Oil, Linden Oil, Lovage Oil, Mandarin Orange Oil, Matricaria Oil, Musk Rose Oil, Nutmeg Oil, Olibanum, Orange Flower Oil, Orange Oil, Patchouli Oil, Pennyroyal Oil, Peppermint Oil, Pine Oil, Pine Tar Oil, Rose Hips Oil, Rosemary Oil, Rose Oil, Rue Oil, Sage Oil, Sambucus Oil, Sandalwood Oil, Sassafras Oil, Silver Fir Oil, Spearmint Oil, Sweet Marjoram Oil, Sweet Violet Oil, Tar Oil, Tea Tree Oil, Thyme Oil, Wild Mint Oil, Yarrow Oil, Ylang Ylang Oil, and the like, as well as mixtures thereof.

Some preferred natural fats and oils include, but are not limited to Avocado Oil, Apricot Oil, Babassu Oil, Borage Oil, Camellia oil, Canola oil, Castor Oil, Coconut oil, Corn Oil, Cottonseed Oil, Evening Primrose Oil, Hydrogenated Cottonseed Oil, Hydrogenated Palm Kernel Oil, Maleated Soybean Oil, Meadowfoam Oil, Palm Kernel Oil, Phospholipids, Rapeseed Oil, Palmitic Acid, Stearic Acid, Linoleic Acid, Rose Hip Oil, Sunflower Oil, Soybean Oil, PROLIPID 141 (proprietary blend of Glyceryl Stearate, Fatty Acids, Lecithin, and Phospholipids from International Specialty Products, Wayne, N.J.) and the like, as well as mixtures thereof.

The term "synthetic fat or oil" is intended to include synthetic fats and oils, esters, silicones, other emollients, and combinations thereof. Examples of suitable synthetic fats or oils include petrolatum and petrolatum based oils, mineral oils, mineral jelly, isoparaffins, polydimethylsiloxanes such as methicone, cyclomethicone, dimethicone, dimethiconol, trimethicone, alkyl dimethicones, alkyl methicones, alkyldimethicone copolyols, organo-siloxanes (i.e., where the organic functionality can be selected from alkyl, phenyl, amine, polyethylene glycol, amine-glycol, alkylaryl, carboxal, and the like), silicones such as silicone elastomer, phenyl silicones, alkyl trimethylsilanes, dimethicone crosspolymers, cyclomethicone, gums, resins, fatty acid esters (esters of $C_6$-$C_{28}$ fatty acids and $C_6$-$C_{28}$ fatty alcohols), glyceryl esters and derivatives, fatty acid ester ethoxylates, alkyl ethoxylates, $C_{12}$-$C_{28}$ fatty alcohols, $C_{12}$-$C_{28}$ fatty acids, $C_{12}$-$C_{28}$ fatty alcohol ethers, propylene glycol esters and derivatives, alkoxylated carboxylic acids, alkoxylated alcohols, fatty alcohols, Guerbet alcohols, Guerbet Acids, Guerbet Esters, and other cosmetically acceptable emollients.

Specific examples of suitable esters include cetyl palmitate, stearyl palmitate, cetyl stearate, isopropyl laurate, isopropyl myristate, isopropyl palmitate, and combinations thereof.

The lipid phase described above may optionally include a ceramide or ceramide derivative, such as glucosylceramides, acylceramide, bovine ceramides, sphingolipid E, and combinations thereof.

The compositions of the present disclosure may contain any other ingredient normally used in cleansing or lotion compositions. Examples of other ingredients may include coloring agents, such as those described above, foam densifying agents, proteins, moisturizing agents, antioxidants, fragrances, antimicrobials, sunscreen agents, esters, emollients, chelating agents, rheology enhancers, anti-aging actives, humectants, oils, solubilizers, vitamins, minerals, and/or other suitable additives, such as those described herein. These ingredients may be included in the composition encapsulated and/or unencapsulated form. Each of these ingredients may be present in an amount effective to accomplish its intended purpose.

Examples of suitable preservatives that may be incorporated into the compositions of this disclosure include EDTA salts, alkyl esters of para-hydroxybenzoic acid, hydantoin derivatives, propionate salts, and a variety of quaternary ammonium compounds. Examples of particular preservatives are iodopropynyl butyl carbamate, phenoxyethanol, methyl paraben, propyl paraben, imidazolidinyl urea, sodium dehydroacetate, propylene glycol, and benzyl alcohol. The type and amount of preservative should be selected so as to be compatible with the intended use of the composition.

Optionally, other rheology enhancers may be included in the composition. Examples of suitable rheology enhancers include combinations of alpha-olefins and styrene alone or in combination with mineral oil or petrolatum, combinations of di-functional alpha-olefins and styrene alone or in combination with mineral oil or petrolatum, combinations of alpha-olefins and isobutene alone or in combination with mineral oil or petrolatum, ethylene/propylene/styrene copolymers alone or in combination with mineral oil or petrolatum, butylene/ethylene/styrene copolymers alone or in combination with mineral oil or petrolatum, ethylene/vinyl acetate copolymers, polyethylene polyisobutylenes, polyisobutenes, polyisobutylene, dextrin palmitate, dextrin palmitate ethylhexanoate, stearoyl inulin, stearalkonium bentonite, distearadimonium hectorite, and stearalkonium hectorite, styrene/butadiene/styrene copolymers, styrene/isoprene/styrene copolymers, styrene-ethylene/butylene-styrene copolymers, styrene-ethylene/propylene-styrene copolymers, (styrene-butadiene) n polymers, (styrene-isoprene) n polymers, styrene-butadiene copolymers, and styrene-ethylene/propylene copolymers and combinations thereof. Specifically, rheology enhancers such as mineral oil and ethylene/propylene/styrene copolymers, and mineral oil and butylene/ethylene/styrene copolymers (Versagel blends from Penreco) are particularly preferred. Also, Vistanex (Exxon) and Presperse (Amoco) polymers are particularly suitable rheology enhancers. Suitable viscosity enhancers include polyolefin resins, lipophilic/oil thickeners, ethylene/vinyl acetate copolymers, polyethylene, silica, silica silylate, silica methyl silylate, colloidal silicone dioxide, cetyl hydroxy ethyl cellulose, other organically modified celluloses, PVP/decane copolymer, PVM/MA decadiene crosspolymer, PVP/eicosene copolymer, PVP/hexadecane copolymer, and combinations thereof.

The compositions may further comprise an aqueous carrier. Water may be present in the compositions in an amount of from about 30% (by weight) to about 95% (by weight).

As discussed herein, the compositions of the present disclosure preferably have a suitable viscosity such that particles and/or other additives may remain suspended in the cleanser for an extended period of time, yet the composition may still be pumped and dispensed from a suitable dispensing unit such as a pump foam dispenser. Preferably, the composition has a resting viscosity of from about 1,000 cps to less than about 50,000 cps, and more preferably from about 3500 cps to about 40,000 cps.

The cleansers of the present invention may have a broad pH range. Typically, the pH of the cleansers will be from about 3 to about 12, preferably from about 4.5 to about 8.5.

A variety of dispensers are known in the art and may be used in conjunction with the products of the present invention. Particularly preferred are foam generating dispensers. Dispensers for forming and dispensing a foam from a foamable liquid are well known. The dispensers may be of several different types including, for example pump foam dispensers, squeeze foam dispensers, and aerosol dispensers. In the case of pump foam and squeeze foam dispensers, foam is generally produced by mixing a foamable liquid and a gas, such as air, whereas aerosol dispensers generate foam using a liquid propellant.

Particularly preferred for use with the compositions of the present disclosure are pump foam dispensers. Conventional pump foam dispensers generally comprise a reservoir for storing a foamable liquid, a dispensing head with a housing containing a pump and a diptube for transferring the foamable liquid from the reservoir into the dispensing head. Foam is created by passing the foamable liquid through a screen material which may be a porous substance such as a sintered material, a wire (plastic or metal) gauze screen or similar structures.

Examples of suitable dispensers are described in, for example, U.S. Pat. Nos. 4,022,351, 4,147,306, and 4,184,615, all of which are herein incorporated by reference. Preferred dispensers include pump foam dispensers available from Airspray International Corporation, such as those described in U.S. Pat. No. 6,053,364, herein incorporated by reference. A particularly preferred dispenser is the Airspray® F2-L7 pump (Airspray International Corporation).

Having described the disclosure in detail, it will be apparent that modifications and variations are possible without departing from the scope of the disclosure defined in the appended claims.

EXAMPLES

The following non-limiting examples are provided to further illustrate the present disclosure.

Example 1

In this example, a foamable, cleansing composition comprising surfactants, a base-sensitive thickener, a swellable clay, and 5 micron diameter particles was produced. The following components were used to prepare the composition:

TABLE 1

| Trade name | Common name | Function | Amount (weight %) |
| --- | --- | --- | --- |
| Water | Water | Aqueous carrier | 86.0000 |
| Aqua SF-1 | Acrylates copolymer | Base-sensitive thickener | 2.0000 |
| Laponite | Laponite | Swellable clay | 1.0000 |
| Potassium hydroxide (KOH) | KOH | Neutralizer | As needed |

TABLE 1-continued

| Trade name | Common name | Function | Amount (weight %) |
| --- | --- | --- | --- |
| Mackadet® EY-191 | Blend of cocamidopropyl betaine, PEG-80 sorbitan laurate, and sodium trideceth sulfate | Surfactant blend | 10.0000 |
| Paragon® II | Blend of propylene glycol, DMDM hydantoin, methylparaben, and propylparaben | Preservative | 0.5000 |
| 5 micron particles | Color encapsulates | Active particle | 0.5000 |

The composition was prepared by adding the laponite to the water and mixing until dispersed. The Aqua SF-1 was then added with mixing until dispersed. The resulting composition was neutralized with KOH, as needed, to a pH of about 7.0. The Mackadeto EY-191 surfactant blend and Paragon® II preservative were added to the composition with mixing until the composition was homogenous. Active particles having a 5 micron diameter were added to the composition with mixing until the particles were dispersed throughout the composition.

The resulting composition was capable of maintaining the particles in suspension for extended periods of time, e.g., for 3 months, but may still be used in connection with a pump foam dispenser, such as an Airspray® pump foam dispenser.

Example 2

In this example, a foamable, cleansing composition comprising surfactants, an acid-sensitive thickener, a swellable clay, and 5 micron diameter particles was produced. The following components were used to prepare the composition:

TABLE 2

| Trade name | Common name | Function | Amount (weight %) |
| --- | --- | --- | --- |
| Water | Water | Aqueous carrier | 68.9950 |
| Structure® Plus | Acrylates/aminoacrylates/ $C_{10-30}$ alkyl PEG-20 itaconate copolymer | Acid-sensitive thickener | 3.0000 |
| Laponite | Laponite | Swellable clay | 1.0000 |
| Sodium laureth sulfate | Sodium laureth sulfate | Surfactant | 16.0000 |
| Mackadet® EY-191 | Blend of cocamidopropyl betaine, PEG-80 sorbitan laurate, and sodium trideceth sulfate | Surfactant blend | 10.0000 |
| Citric acid | Citric acid | Neutralizer | 0.0050 |
| Paragon® II | Blend of propylene glycol, DMDM hydantoin, methylparaben, and propylparaben | Preservative | 0.5000 |
| 5 micron particles | Colored encapsulates | Active particle | 0.5000 |

The composition was prepared by adding the laponite to the water and mixing until dispersed. The Structure® Plus thickener was then added with mixing until dispersed. The resulting composition was neutralized with citric acid to a pH of about 5.5. The sodium laureth sulfate, Mackadet® EY-191 surfactant blend, and Paragon® II preservative were added to the composition with mixing until the composition was homogenous. Active particles having a 5 micron diameter were added to the composition with mixing until the particles were dispersed throughout the composition.

The resulting composition was capable of maintaining the particles in suspension for extended periods of time, e.g., about 3 months, but may still be used in connection with a pump foam dispenser, such as an Airspray® pump foam dispenser.

Example 3

In this example, a foamable, cleansing composition comprising surfactants, a cellulosic thickener, a swellable clay, and 5 micron diameter particles was produced. The following components were used to prepare the composition:

TABLE 3

| Trade Name | Common Name | Function | Amount (weight %) |
|---|---|---|---|
| Water | Water | Aqueous carrier | 74.8000 |
| Laponite | Laponite | Swellable clay | 1.0000 |
| Xanthan gum | Xanthan gum | Thickener | 0.2000 |
| Sodium laureth sulfate | Sodium laureth sulfate | Surfactant | 16.0000 |
| Mackadet® EY-191 | Blend of cocamidopropyl betaine, PEG-80 sorbitan laurate, and sodium trideceth sulfate | Surfactant blend | 5.0000 |
| Methyl gluceth-20 | Methyl gluceth-20 | Humectant | 2.0000 |
| Citric acid | Citric acid | Neutralizer | As needed |
| Paragon® II | Blend of propylene glycol, DMDM hydantoin, methylparaben, and propylparaben | Preservative | 0.5000 |
| 5 micron particles | Colored encapsulates | Active particle | 0.5000 |

The formulation was prepared by adding the laponite and xanthan gum to the water with mixing until dispersed. The resulting composition was adjusted with citric acid to a pH of approximately 7.0. The sodium laureth sulfate, and Mackadeto EY-191 surfactant blend, and Paragon® II preservative were added to the composition with mixing until the composition was homogenous. Active particles having a 5 micron diameter were added to the composition with mixing until the particles were dispersed throughout the composition.

The resulting formulation was capable of maintaining the particles in suspension for extended periods of time, e.g., about 3 months, but may still be used in connection with a pump foam dispenser, such as an Airspray® pump foam dispenser.

Example 4

In this example, a formulation comprising surfactants, a base-sensitive thickener, and 5 micron diameter particles, but lacking a swellable clay, was produced. The following components were used to prepare the composition:

TABLE 4

| Trade Name | Common Name | Function | Amount (weight %) |
|---|---|---|---|
| Water | Water | Aqueous carrier | 76.0000 |
| Aqua SF-1 | Acrylates copolymer | Base-sensitive thickener | 6.0000 |
| Sodium laureth sulfate | Sodium laureth sulfate | Surfactant | 17.0000 |
| Paragon® II | Blend of propylene glycol, DMDM hydantoin, methylparaben, and propylparaben | Preservative | 0.5000 |
| 5 micron particles | Colored encapsulates | Active particle | 0.5000 |

The composition was prepared by adding the Aqua SF-1 to the water and mixing until dispersed. The resulting composition was neutralize with KOH, as needed, to a pH of about 7.0. The sodium laureth sulfate and Paragon® II preservative were added to the composition with mixing until the composition was homogenous. Active particles having a 5 micron diameter were added to the composition with mixing until the particles were dispersed throughout the composition.

The resulting composition was capable of maintaining the particles in suspension for extended periods of time, e.g., about 3 months. However, unlike the compositions produced in Examples 1-3, this composition did not produce foam when used in connection with a pump foam dispenser, such as an Airspray® pump foam dispenser. This may be because of the high viscosity of the composition and/or because the composition lacks the necessary shear thinning nature.

Example 5

In this example, the viscosity under shear of the foamable cleansing composition produced in Example 1 was compared to a commercially available foaming hand soap (Cleanteam™ Foaming Hand Soap), and a commercially available suspended bead hand soap (Bath & Body Works® Pink Grapefruit Antibacterial Hand Soap). The viscosity (in centipoise) of the soaps was measured under various shear rates using a RheoStress RS1 rheometer (available from Thermo Electric Corporation, Madison Wis.), with a 2° angle measurement, titanium cone and plate. The results are shown in Table 5 and FIG. 1.

TABLE 5

| | Viscosity (cP) | | |
|---|---|---|---|
| Shear (1/sec) | Commercial suspended bead hand soap | Commercial foaming hand soap | Example 1 cleanser |
| 0.373 | 16,000 | 4280 | 22,580 |
| 2.646 | 7648 | 683 | 3174 |
| 4.759 | 5000 | 218 | 1850 |
| 9.963 | 3443 | 168 | 1017 |
| 15.01 | 2766 | 169 | 718 |

As can be seen from these results, the composition produced in Example 1 has a higher viscosity under low shear, as compared to both the commercial suspending hand soap and the commercial foaming hand soap. The viscosity of all three samples decreased as shear rate increased, with the viscosity of the Example 1 composition being less than the commercial suspending hand soap but greater than the commercial foaming hand soap.

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the disclosure are achieved and other advantageous results attained.

As various changes could be made in the above products without departing from the scope of the disclosure, it is intended that all matter contained in the above description shall be interpreted as illustrative and not in a limiting sense.

What is claimed is:

1. A cleansing composition comprising from about 0.1% (by weight) to about 40% (by weight) of a foaming agent, from about 0.01% (by weight) to about 5% (by weight) of a thickener, from about 0.01% (by weight) to less than about 5% (by weight) of a swellable clay, and particles having a particle size of from about 150 microns to about 4 millimeters suspended in the composition, wherein the particles comprise encapsulated additives and wherein the composition has a viscosity of from about 3,500 cps to about 40,000 cps and a pH of from about 4.5 to about 8.5.

2. The composition of claim 1 wherein the foaming agent is a surfactant selected from the group consisting of anionic surfactants, amphoteric surfactants, cationic surfactants, zwitterionic surfactants, non-ionic surfactants, and combinations thereof.

3. The composition of claim 1 wherein the thickener is selected from the group consisting of cellulosic thickeners, gums, acrylic based polymers, and combinations thereof.

4. The composition of claim 3 wherein the thickener is selected from the group consisting of xanthan gum, agar, alginates, carrageenan, furcellaran, guar, cationic guar, gum arabic, gum tragacanth, karaya gum, locust bean gum, dextran, starch, modified starches, gellan gum, carboxymethylcellulose, hydroxypropylcellulose, hydroyethylcellulose, propylene glycol alginate, hydroxypropyl guar, amylopectin, cellulose gum, chitosan, modified chitosan, hydroxypropyl methylcellulose, microcrystalline cellulose, silica, fumed silica, colloidal silica, dehydroxanthan gum, non-acrylic based carbomers, and combinations thereof.

5. The composition of claim 3 wherein the thickener is a cellulosic thickener or gum, the composition comprising from about 0.01% (by weight) to about 2% (by weight) thickener.

6. The composition of claim 3 wherein the thickener is an acrylic based polymer, the composition comprising from about 0.1% (by weight) to about 5% (by weight) acrylic based polymer.

7. The composition of claim 1 wherein the thickener is selected from the group consisting of an acid-sensitive thickener, a base-sensitive thickener, and combinations thereof.

8. The composition of claim 1 wherein the swellable clay is selected from the group consisting of bentonite, laponite, hectorite, montmorillonite, beidelite, saponite, stevensite, magnesium aluminum silicate, and combinations thereof.

9. The composition of claim 1 comprising from about 0.01% (by weight) to about 40% (by weight) particles.

10. The composition of claim 1 wherein the particles further comprise colored particles.

11. The composition of claim 1 further comprising from about 0.5% (by weight) to about 15% (by weight) of a lipid phase.

12. A composition comprising from about 0.01% (by weight) to about 5% (by weight) of a thickener, from about 0.01% (by weight) to about 10% (by weight) of a swellable clay, and particles having a particle size of from about 150 microns to about 4 millimeters suspended in the composition, wherein the particles comprise encapsulated additives, and wherein the composition has a viscosity of from about 3,500 cps to about 40,000 cps and a pH of from about 4.5 to about 8.5.

13. The composition of claim 12 wherein the particles further comprise colored particles.

14. The composition of claim 12 wherein the composition comprises from about 0.01% (by weight) to about 40% (by weight) particles.

15. The composition of claim 12 further comprising from about 0.5% (by weight) to about 15% (by weight) of a lipid phase.

16. A composition comprising from about 0.01% (by weight) to about 5% (by weight) of a thickener, from about 0.01% (by weight) to about 10% (by weight) of a swellable clay, and colored particles suspended therein, wherein the colored particles have a particle size of about 300 microns to about 4 millimeters and the composition has a viscosity of from about 3,500 cps to about 40,000 cps and a pH of from about 4.5 to about 8.5.

* * * * *